US006580507B2

United States Patent
Fry et al.

(10) Patent No.: US 6,580,507 B2
(45) Date of Patent: Jun. 17, 2003

(54) SINGLE SOURCE, SINGLE DETECTOR CHIP, MULTIPLE-LONGITUDINAL CHANNEL ELECTROMAGNETIC RADIATION ABSORBANCE AND FLUORESCENCE MONITORING SYSTEM

(75) Inventors: Robert C. Fry, Omaha, NE (US); Michael R. Dyas, Waterloo, NE (US)

(73) Assignee: SD Acquisition Inc., Omaha, NE (US)

(*) Notice: Subject to any disclaimer, the term of this patent is extended or adjusted under 35 U.S.C. 154(b) by 229 days.

(21) Appl. No.: 09/797,932

(22) Filed: Mar. 2, 2001

(65) Prior Publication Data

US 2001/0035947 A1 Nov. 1, 2001

Related U.S. Application Data

(60) Provisional application No. 60/187,175, filed on Mar. 2, 2000.

(51) Int. Cl.$^7$ .................................................. G01N 21/00
(52) U.S. Cl. ......................................... 356/436; 356/440
(58) Field of Search ................................. 356/244, 436, 356/440

(56) References Cited

U.S. PATENT DOCUMENTS

| | | | |
|---|---|---|---|
| 3,579,105 A | 5/1971 | Scott ............................ 324/99 |
| 3,790,798 A | 2/1974 | Sternberg et al. ........... 250/345 |
| 3,986,776 A | 10/1976 | George ......................... 356/88 |
| 4,079,256 A | 3/1978 | Ford et al. ................... 250/343 |
| 4,084,248 A | 4/1978 | Scott ............................ 364/571 |
| 4,577,106 A | 3/1986 | Fukasawa et al. ........... 250/347 |
| 4,832,491 A | 5/1989 | Sharpe et al. ................ 356/326 |
| 4,895,445 A | 1/1990 | Granger ....................... 356/328 |
| 5,166,755 A | 11/1992 | Gat .............................. 356/419 |
| 5,324,401 A | * 6/1994 | Yeung et al. ................. 356/344 |
| 5,491,344 A | * 2/1996 | Kenny et al. ................. 356/73 |
| 5,498,324 A | * 3/1996 | Yeung et al. ................. 356/344 |
| 5,584,982 A | * 12/1996 | Dovichi et al. .............. 356/344 |
| 5,721,613 A | 2/1998 | Linowski et al. ........... 356/318 |
| 5,763,277 A | 6/1998 | Zhu et al. .................... 436/172 |
| 5,792,663 A | 8/1998 | Fry et al. ..................... 436/73 |
| 5,815,276 A | 9/1998 | Fry ............................. 356/437 |
| 5,825,478 A | * 10/1998 | Wilcox et al. ............... 356/73 |
| 5,903,348 A | * 5/1999 | Melman et al. ............. 356/344 |
| 6,008,055 A | 12/1999 | Zhu et al. .................... 436/172 |
| 6,084,667 A | * 7/2000 | Melman et al. ............. 356/246 |
| 6,171,865 B1 | * 1/2001 | Weigl et al. .................. 436/52 |
| 6,181,418 B1 | 1/2001 | Palumbo et al. ............ 356/328 |
| 6,192,168 B1 | * 2/2001 | Feldstein et al. ............ 385/12 |
| 6,222,619 B1 | * 4/2001 | Herron et al. ................ 356/39 |
| 6,384,912 B2 | * 5/2002 | Kraus et al. ................. 356/246 |
| 6,437,345 B1 | * 8/2002 | Bruno-Raimondi et al. ..... 250/458.1 |
| 6,445,448 B1 | * 9/2002 | Melman et al. ............. 356/246 |

* cited by examiner

Primary Examiner—Michael P. Stafira
Assistant Examiner—Juan D Valentin, II
(74) Attorney, Agent, or Firm—James D. Welch (57) ABSTRACT

Disclosed is a multiple longitudinal flow cell channel electromagnetic radiation absorption or fluorescence monitoring system wherein a source of electromagnetic radiation is positioned to input electromagnetic radiation to each of the longitudinal flow cell channels, and wherein a single low cost, low drift, preferably linear and sensitized to UV, array detector system is positioned to directly simultaneously monitor electromagnetic radiation from at least two of the longitudinal flow cell channels, at different locations thereupon.

2 Claims, 7 Drawing Sheets

FIG. 7

SINGLE SOURCE, SINGLE DETECTOR CHIP, MULTIPLE-LONGITUDINAL CHANNEL ELECTROMAGNETIC RADIATION ABSORBANCE AND FLUORESCENCE MONITORING SYSTEM

This Application is a CIP of Provisional Application Serail No. 60/187,175 filed Mar. 2, 2000.

TECHNICAL FIELD

The present invention relates to absorbance and fluorescence electromagnetic radiation monitoring systems, and more specifically to photometry, spectrometry and spectrophotometry systems which comprise a sequential combination of a single source of electromagnetic radiation, a multiple longitudinal flow cell channel containing system and a single low cost, low drift electromagnetic radiation detector chip.

BACKGROUND

Electromagnetic radiation absorbance and fluorescence monitoring systems which comprise a source of electromagnetic radiation and at least one detector system, wherein electromagnetic radiation of known incident radiant power ($P^0$) is caused to interact with a sample, (often situated in a longitudinal flow cell channel), and wherein the results of said interaction are detected by said detector system, are well known. Samples which can be monitored thereby include:

at least partially transparent solids;

liquids;

suspensions;

gases;

vapors; and analyte dissolved or dispersed in carrier gas or liquid.

For instance, in use, partially transparent solid or fluid, (eg. gas, vapor, liquid, fluid suspension etc. typically flowed into or through a containing cell), samples can be placed in the path of an electromagnetic beam, and incident Radiant Power ($P^0$) of electromagnetic radiation passed therethrough is attenuated, relative to ($P^0$), thereby via absorption, which is dependent on atomic and/or molecular structure of analytes contained within the sample and present carrier gas etc. Said attenuation is related to the concentration of analytes in the sample present by Beer's Law, and is evidenced by exiting electromagnetic radiation of reduced radiant power (P).

Continuing, electromagnetic radiation absorption monitoring systems may be of either "Single Beam" or "Double Beam" configuration. "Single Beam" systems utilize only one flow channel, (per analyte), and incident radiant power is measured by first introducing blank carrier "reference" medium and measuring radiant power out ($P^0$) During an analysis procedure this is followed by entry of "reference" medium which further contains sample analyte, and the measurement of transmitted radiant power (P). "Single Beam" photometry or spectrophotometry systems then require that the same flow cell channel be utilized in determining both ($P^0$) and (P). With ($P^0$) and (P) so determined analyte absorbance (A) is calculated as a negative Logarithmic ratio:

$$A = -\text{Log}((P)/(P^0));$$

where the ratio $(P)/(P^0)$ is termed the Transmittance (T). The magnitude of (A) is further related to analyte structural properties through its wavelength dependent molar absorptivity (a or $\epsilon$), to the flow cell channel length (b), and to analyte concentration (C) by Beer's Law:

$$A = abC;$$

or $$A = \epsilon bC.$$

Thus in order to calculate concentration (C):

$$C = A/ab = A/\epsilon b$$

(a) or ($\epsilon$) and (b) must be known at an isolated wavelength at which (A) is calculated from:

$$A = -\text{Log}(T) = -\text{Log}((P)/(P^0)).$$

(It is noted that (a) and/or (b) can be determined by standard calibration procedures).

Note that any procedure which involves a ratio $(P)/(P^0)$ inherently provides for canceling out long term temporal variations of source intensity and detector response. However short term source drift and fluctuation within the time frame between flow exchange of blank carrier and analyte containing carrier, hence if ($P^0$) and (P) are measured with a significant intervening time, (eg. typically minutes), therebetween, and system drift and/or fluctuation occurs in that time period, the effects will not be canceled and error will be introduced into results achieved by the use of a single beam system.

As a result of problems inherent in use of "Single Beam" applications, "Double Beam" absorbance measurement is commonly employed wherein ($P^0$) and (P) are measured simultaneously or with a very short time period, (eg. milliseconds), therebetween. Additionally, "Double Beam" systems do not require physical medium exchange within a given flow cell channel.

Two basic versions of "Double Beam" electromagnetic radiation absorption monitoring systems exist and are termed "double beam in time" and "double beam in space" systems respectively.

In the first version, (ie. a double-beam-in-time system), a single detector is typically used, and a beam of electromagnetic radiation provided by said source thereof is caused to exit said source of electromagnetic radiation, and is sequentially in either order:

caused to pass through a sample in a flow cell channel which sample is typically dispersed or dissolved in a carrier gas or liquid and enter said detector system where (P) is measured; and alternatively, caused to pass directly from said source of electromagnetic radiation and enter said detector system without passing through said sample, (optionally through a second reference flow channel which contains a blank carrier medium), and enter said detector where ($P^0$) is measured.

Note that the single Detector is caused to switch between monitoring (P) and ($P^0$) in a synchronized alternating manner so as to keep the measurements separate, and such is typically accomplished at high speed. Forming a ratio of (P) and ($P^0$) signals sequentially developed by the detector then provides indication of the absorbance (A) of the sample, and except for the effects of very short temporal fluctuations, (shorter than the switching speed between the detector monitoring (P) and ($P^0$) signals), all system parameters are normalized by said ratioing, leaving final dependency of (A) solely on a, b and C. Note that where ($P^0$) is determined where a blank carrier medium is placed in the reference electromagnetic beam pathway, said ratioing approach also serves to cancel the absorption effect of the carrier medium.

In the second version, (ie. a double-beam-in-space system), two detectors are typically utilized, and a beam of electromagnetic radiation provided by the source thereof is permanently divided into two fixed paths, (eg. by a beam splitter), and:

one portion is caused to pass directly from the source of electromagnetic radiation through a non-sample containing reference flow cell and into one detector, such that attenuation is dependent only on ambient, (eg. blank carrier gas);

while the other portion is simultaneously caused to pass through the a sample containing flow cell and into the other detector.

(Note that two optical beams and two flow cell channel means are typically present, in one of which sample is caused to be present, (thereby facilitating measurement of (P)), while the other has no sample present and serves as reference, (thereby facilitating measurement of ($P^o$)).

Forming a ratio of the signals (($P$)/($P^o$)) from the two detectors provides indication of the Transmittance (T) and absorbance (A) of the sample, and normalizes essentially all temporally variant system parameters, as well as canceling the absorbance of the reference medium. Differences, however, in the inherent electronic gain and chromatic response etc. of the two separate detector systems to similar input signals can enter errors into results achieved by this approach.

The first version of the electromagnetic radiation absorption monitoring systems, (ie. "double beam in time"), is then subject to errors which develop because of very short term fluctuations in the source of electromagnetic radiation which vary with time more quickly than optical beam switching, and the second version, (ie. "double beam in space"), is subject to errors which result from the fact that two different detector systems are utilized, and that said detectors can have different operational response, (eg. gain, chromaticity, etc.), to the same input thereto.

At this point, with an eye to the present invention, it should be appreciated that a Double-Beam-In-Space system which comprised a single source of electromagnetic radiation, a multiplicity of flow cell channels, and a single detector would provide utility.

Continuing, in both Double-Beam-In-Space and Double-Beam-In Time versions of electromagnetic radiation absorbance monitoring systems, it is possible to specifically monitor isolated wavelengths of a multiplicity of wavelengths by incorporating wavelength separation means such as, for instance, diffraction grating, wavelength filtration, prismatic, dispersion or interferometric wavelength separation. Where wavelength separation is achieved by filtration the system is typically called a double beam photometer, and where grating or prismatic dispersion, with slit width isolation of dispersed radiation, is utilized, the system is typically termed a spectrophotometer.

It has already been noted that a typical approach to describing sample caused electromagnetic radiation radiant power attenuation involves use of Beer's Law, and that involves forming a negative logarithmic ratio of sample (P) and reference ($P^o$) signals. Parameters affecting attenuation are cell length (b), wavelength dependent absorptivity coefficient (a or $\epsilon$) of analyte, and sample analyte concentration (C).

Further, it is known to use electromagnetic radiation to cause fluorescence in sample analyte, with said fluorescence being then detected as a means to identifying the fluorescing sample analyte. Often in such systems excitation electromagnetism is entered obliquely to a flow cell longitudinal channel axis and induced electromagnetic radiation fluorescence wavelengths are monitored by a detector obliquely oriented to receive said fluorescence from a direction which is other than parallel to the longitudinal axis direction.

Known relevant Patents include a Palumbo et al., U.S. Pat. No. 6,181,418 which describes a concentric spectrometer system which includes application of a two-dimensional area array detector.

Another U.S. Pat. No. 5,166,755 to Gat, describes a spectroscopic apparatus which uses a spectrum resolving sensor containing an opto-electronic monolithic array of photosensitive elements.

A Patent to Granger, U.S. Pat. No. 4,895,445, describes a spectrophotometer system with a bulb means for illuminating a sample, in combination with a CCD array detector system.

A Patent to Linowski et al., U.S. Pat. No. 5,721,613 describes a fluorescence spectrometer and is disclosed for general purposes.

A Patent to U.S. Pat. No. 4,832,491 to Sharpe et al describes a method of using electromagnetic radiation to investigate a sample, involving using a monochromator to set a wavelength, obtaining reference data, obtaining sample data, forming a ratio of the sample and reference data, and repeating said steps for additional wavelengths.

Another U.S. Pat. No. 3,790,798 to Sternberg et al., describes a single beam system wherein reference data is obtained with filters in place in said system which pass wavelengths other than those which are absorbed by a sample analyte, (eg. gas in a sample containing cell). Said 798 Patent describes obtaining both sample and reference data and forming a ratio therebetween.

A Patent to Fukasawa et al., U.S. Pat. No. 4,577,106, describes a double beam spectrophotometer which contains means for allowing acquisition of dark, reference, sample and reference data.

A Patent to George, U.S. Pat. No. 3,986,776 describes baseline compensation in a double beam spectrophotometer.

U.S. Pat. No. 4,079,256 to Ford et al., describes a double-beam system in which two evaluations are combined to produce a derived reference signal in a situation wherein sample and reference signals do not occur at the same time, because a single spectrophotometer detector system it utilized.

U.S. Pat. Nos. 4,084,282 and 3,579,105 to Scott describe double beam systems in which in the calibration run two beams are compared at each wavelength and adjustment disparities are calculated, said adjustments being applied during sample runs.

Patent to Fry, U.S. Pat. No. 5,792,663, is identified and incorporated herein by reference as it describes a high efficiency continuous flow through fractional-volatilization separator system and method for use in detection of mercury, via, for example, double-beam-in-space filter photometry.

U.S. Pat. No. 5,815,276 to Fry is disclosed as it describes a long path absorbance-cell imaging system with provision for decreasing sensitivity to element parameter change.

Patent to Zhu et al, U.S. Pat. Nos. 5,763,277 and 6,008,055 are identified as relevant to fluorescence monitoring systems. Said systems facilitate entering excitation radiation axially to a longitudinal flow channel and the measuring of resulting fluorescence with a detector oriented obliquely to said longitudinal flow channel.

Even in view of the known prior art, need remains for a multiple channel absorbance and fluorescence monitoring system which uses a single low cost, low drift detector for use in, for instance, simultaneously monitoring a plurality of sample, and/or reference, related beams of electromagnetic radiation. An optimum solution would involve use of a single, low cost, detector system, which single detector system is comprised of a multiplicity of substantially identical pixel detection elements on one monolithically produced semiconductor chip, such that various groupings of said pixels can be "binned" and then utilized to detect electromagnetic radiation from specific beams of electromagnetic radiation.

DISCLOSURE OF THE INVENTION

Low cost, linear (one dimensional), silicon photo-diode arrays (PDA) and silicon charge coupled devices (CCD) arrays have long been available for application is Fax machines, in bar code reading systems, and have been applied in detection of spectrally dispersed radiation in single beam prism spectrometers and single beam grating spectrometers. Two dimensional Photo-diode (PDA) and Charge Coupled Device (CCD) arrays are also available at higher cost. The present invention makes use of such linear (preferred) or two dimensional single detector chip arrays of such (PDA's) or (CCD's) to enable simultaneous direct monitoring of sample and/or reference electromagnetic beams in a multiple-flow-cell-channel electromagnetic radiation absorbance monitoring system, the individual flow cell channels of which are individually directly provided electromagnetic radiation which is sequestered from a single source.

As a specific example, one low cost linear array, which is a applicable to use in the present invention, contains 2048 pixels. In use pixels #100–190 700 can be sequestered for use in detecting one electromagnetic beam, pixels #701–#1300 can be set aside as "dark space" and pixels #1301–#2000 can be sequestered for use in detecting a second electromagnetic beam. The signals from pixels #100–#700 can be summed, as can be signals from pixels #1301–#2000 to provide separate sample (P) and reference ($P^0$) "radiant powers", and a ratio can be formed from the results to mediate formation of a negative logarithmic ratio. Of course smaller groupings of pixels can be identified for detection of a larger number of electromagnetic beams, in either a one or two dimensional array.

It is noted generally that where sensing is simultaneous in time, the effects of such as very short term electromagnetic radiation source fluctuations can be canceled in a formed ratio therebetween. This is particularly true where pixels on a single detector chip are utilized as they are generally well matched to one another, and, further, being on a single physical chip, tend to be subject to, and respond similarly to external thermal influences.

It is also noted that where a grouping of pixels receives input electromagnetic radiation from only one cell path out of a plurality of cell paths and signals from said cell paths are summed, said grouping can be termed "binned", and binning within sample and reference detecting groups improves the signal to noise ratio of said groups by a factor of the square-root-of-N, where N is the number of pixels in the group. Further, where a grouping of pixels includes some perimeter pixels which might receive overlapping input electromagnetic radiation from more than one cell, binning involves excluding said perimeter pixels.

More specifically then, the present invention is a multiple flow cell channel electromagnetic radiation absorbance monitoring system comprising:
a source of electromagnetic radiation;
a multiple-longitudinal flow cell channel system; and
a detector chip;
longitudinal axes of said multiple-longitudinal flow cell channels in said multiple-longitudinal flow cell channel system being oriented substantially parallel to one another;
where the multiple-longitudinal flow cell channel system is preferably of monolithic construction comprised of a plurality of bores in a mass of material, and
wherein the detector chip comprises a multiplicity of detector elements in a single substrate; and
wherein said source of electromagnetic radiation has dimensions sufficient to simultaneously directly enter electromagnetic radiation to at least two longitudinal flow cell channels in said multiple-longitudinal flow cell channel system; and
wherein said detector chip is of sufficient dimensions to simultaneously directly receive electromagnetic radiation from at least said at least two longitudinal flow cell channels in said multiple-longitudinal flow cell channel system, onto at least two separate groupings of pixels on said detector chip.

While all longitudinal flow cell channels of a present invention multiple channel electromagnetic radiation absorbance monitoring system will typically comprise means for flowing analyte containing fluid, (ie. a gas or liquid), through a portion thereof, or means for positioning an at least partially transparent solid in the pathway of an electromagnetic beam of radiation, it is noted that one or more longitudinal flow cell channel(s) which are used for reference, can be optionally sealed or otherwise optionally not have means for flowing analyte containing fluid through a portion thereof, or means for positioning an at least partially transparent solid present. Alternatively one or more longitudinal channels which are used for reference may contain reference medium either statically or flowing.

While not preferred, a source of electromagnetic radiation of limited dimensions can be applied where rays therefrom are optically subdivided and provided separately to individual longitudinal flow cell channels.

The present invention can also be described as a multiple-channel electromagnetic radiation absorbance monitoring system comprising:
a source of electromagnetic radiation;
a multiple-longitudinal flow cell channel system; and
a detector chip;
longitudinal axes of said multiple-longitudinal flow cell channels in said multiple-longitudinal flow cell channel system being oriented substantially parallel to one another;
wherein said source of electromagnetic radiation has dimensions sufficient to simultaneously directly enter electromagnetic radiation to at least two longitudinal flow cell channels in said multiple-longitudinal flow cell channel system; and
wherein said detector chip has sufficient dimensions to simultaneously directly receive electromagnetic radiation from at least said at least two longitudinal flow cell channels in said multiple-longitudinal flow cell channel system; and
wherein each longitudinal flow cell channel of multiple-longitudinal flow cell channel system has means for directly entering electromagnetic radiation from said source of electromagnetic radiation, and wherein at least some of said longitudinal flow cell channels also have means for flowing analyte containing fluid through a portion thereof in the pathway of said electromagnetic radiation. Further, each longitudinal flow cell channel in said multiple-longitudinal flow cell channel cell system is oriented to direct electromagnetic radiation entered thereinto from said source of electromagnetic radiation, after it passes through said longitudinal flow cell channel, directly onto said detector chip such that electromagnetic radiation passing through at least two longitudinal flow cell channels arrive at said detector chip at substantially different locations thereupon.

Again, while not preferred, a source of electromagnetic radiation of limited dimensions can be applied where rays therefrom are optically subdivided and provided separately to individual longitudinal flow cell channels.

A preferred embodiment of said multiple channel electromagnetic radiation absorbance monitoring system has at least two, (typically more, and nine (9) which will be used as a non-limiting example elsewhere herein), longitudinal flow cell channels bored through a monolithic mass of material, at least one of said longitudinal flow cell channels optionally having two lengths of quartz rod, (eg. with optically polished flat ends), embedded therewithin in a manner which seals a length (b) of said longitudinal flow cell channel therebetween, and each of said at least two longitudinal flow cell channels further having, as means for entering and exiting electromagnetic radiation selections from the group consisting of:

sapphire ball/lens and optional lengths of quartz rod, (typically with polished ends);

fused silica lens element;

glass lens element;

plastic lens element fiber optics;

embedded therein, one at each end thereof. Means for flowing analyte containing fluid through each longitudinal flow cell channel preferably comprise two access channels which have oblique to perpendicular access to a longitudinal flow cell channel, centrally located within said flow cell channel length (b). Further, a sapphire ball/lens, for instance, at one end of each of said at least two longitudinal flow cell channels is positioned to receive and collimate, or at least partially collimate, electromagnetic radiation directly from said source of electromagnetic radiation, and the sapphire ball/lens at the other end of said at least two longitudinal flow cell channels is positioned to de-collimate, (ie. focus), and direct electromagnetic radiation directly onto said detector chip.

Variations of the described multiple channel electromagnetic radiation absorbance monitoring system provide for the absence of the quartz rods such that, for instance, sapphire ball/lens remain and perform the flow sealing function, preferably immediately adjacent to the flow entry and exit ports. Further, it is possible to eliminate both the sapphire ball/lens and quartz rods and apply fiber optics to both seal and direct electromagnetic radiation to and from both ends of longitudinal flow cell channels. The resulting embodiment of said multiple channel electromagnetic radiation absorbance monitoring system can then be described as having at least two, (typically more, and nine (9) which will be used as a non-limiting example elsewhere herein), longitudinal flow cell channels present through a monolithic mass of material, at least one of said at least two longitudinal flow cell channels having a selection from the group consisting of:

sapphire ball/lens and optional lengths of quartz rod, (typically with polished ends);

fused silica lens element;

glass lens element;

plastic lens element fiber optics;

of any functional focusing shape, (eg. spherical, hemispherical, plano-convex, focusing concave-convex), embedded in both ends thereof in a manner which seals a length (b) of said longitudinal flow cell channel therebetween. Means for flowing analyte containing fluid through longitudinal flow cell channels preferably comprise two access/exit channels which have oblique to perpendicular access to a longitudinal flow cell channel, and access is centrally located in the longitudinal flow cell channels, (preferably adjacent to the seal points). Further, a sapphire ball/lens or fiber optic at one end of each of said at least two longitudinal flow cell channels is positioned to receive and collimate electromagnetic radiation from said source of electromagnetic radiation, and the sapphire ball/lens or fiber optic at the other end of said at least two longitudinal flow cell channels is positioned to de-collimate, (ie. focus), and direct electromagnetic radiation directly to said detector chip.

While any functional source of electromagnetic radiation can be applied, in the present invention multiple channel absorbance monitoring system, an example of such a source of electromagnetic radiation is a low pressure mercury (Hg) vapor discharge lamp, emitting a plurality of wavelengths, of which 253.7 nm (nominally 254 nm), is one wavelength.

The present invention multiple channel electromagnetic radiation absorbance monitoring system can further comprise a mask, (eg. comprising at least two holes), which is positioned between said source of electromagnetic radiation and the for instance, sapphire balls/lenses present at the end of said at least two longitudinal flow cell channels, which mask is positioned to receive electromagnetic radiation from said source of electromagnetic radiation, such that holes in said at mask each isolate and pass electromagnetic radiation to only one sapphire ball/lens or alternative means for entering electromagnetism into said longitudinal flow cell channels.

Additionally, any present invention multiple channel electromagnetic radiation absorbance monitoring system can further comprise an electromagnetic radiation wavelength filter adjacent to said mask, or anywhere between the source of electromagnetic radiation and the detector chip.

Suitable detector chips include a linear 2048 pixel Sony CCD array, but acceptable detector chips include selections from the group consisting of a linear or two dimensional:

128;

256;

512;

2048;

3072; and

4096;

pixel, or other commonly available CCD or photo-diode pixel array. Said detector chips, it is noted, are typically suitable for use only in detecting visible wavelengths, however, said detector chips can be thinly coated, (eg. 500 to 10,000 Angstroms), with a lumagen or other fluorophore at the input to the detector elements, and preferably directly on the detector elements, to facilitate UV sensitivity and mediate consistency of wavelength input to detector pixels. Such is particularly beneficial if the detector array was produced under conditions yielding a silicon monoxide overlayer, (as occurs via an oxidation during certain steps of "unprotected" chip fabrication) atop thereof. It is noted that the fluorophore has been found to be less necessary where wavelengths greater than about 360 nm are utilized, and where the oxidation layer mentioned is prevented from forming during "protected" chip manufacture. (It is specifically noted, however, that most readily available low cost detector chips which are applied to Fax and Bar Code reading systems are sensitive in the Visible wavelength range, but are not sensitive in the UV. In the context of a present invention, the practice of applying the lumagen or other fluorophore at the input to the detector elements to extend their application into the UV has been found to be particularly beneficial). A suitable Lumagen is manufactured by BASF, is identified by the Registered Trade mark "LUMOGEN", and called "Brilliant Yellow", "Fluorescent Yellow" or Methine Yellow" and is identified by the Number "S 0790", and has the CAS or CA Registry No. is 2387-03-3. It is chemically identified by the formula (C22H16N2O2) having molecular weight of 340.

Suitable materials in which to form longitudinal flow cell channels include:

PEEK, (other functionally acceptable machinable polymers to be considered equivalent);

fused silica;

glass;

titanium; and passivated stainless steel;

and a suitable approach to forming said longitudinal flow cell channels is by machine boring. It should be understood however, that a typical bore diameter of 0.44 mm, of 1.4 cm in length, can not practically be directly machined into fused silica, glass, titanium or passivated stainless steel, but rather a larger diameter bore must be machined, and said larger bore fitted with a tube which has a desired diameter bore therein. An alternative which is within the scope of the present invention is to provide an array of separate tubes which are mounted in a fixed position in relation to one another.

It is again noted that while the present invention is easily applied as a double-beam-in-space electromagnetic radiation absorbance monitoring system, one preferred embodiment in fact provides for more than two "beams" in the form of causing electromagnetic radiation to pass through multiple analyte containing fluid containing longitudinal flow cell channels. In use, however, signals mediated in development by any of said longitudinal flow cell channels are typically ratioed with a signal mediated in development by a reference longitudinal flow cell channel in which may optionally be present reference carrier media, (or not), but in which is not present analyte containing fluid, (thus the terminology "double-beam-in-space", or "multiple-beam-in-space").

It should be appreciated that by using a single chip based detector system which allows sequestering pixels therein into multiple "binned" (ie. they receive electromagnetic radiation form only one longitudinal flow cell channel), groups, that problems associate with using different detectors, (which can respond differently to like input signals), as is typical in double-beam-in-space electromagnetic radiation absorbance monitoring systems, are minimized.

It is to be further understood that the present invention may employ, but does not necessarily require use of a beam-splitting means to provide multiple beams of electromagnetic radiation. In a preferred embodiment, however, a source of electromagnetic radiation of sufficient physical dimension to simultaneously directly provide electromagnetic radiation to all longitudinal flow cell channels directly is utilized. (Note, the electromagnetic radiation provided to a longitudinal flow channel can be termed a "beam" even though it is derived directly from a single large area source). In other embodiments beam expansion, beam splitting or fiber optical subdivision of a beam of electromagnetism from a source thereof can be applied.

It is specifically again noted that at least two longitudinal flow cell channels are recited as present in one embodiment of the present invention termed a double-beam-in-space electromagnetic radiation absorbance monitoring system. However, preferred embodiments may have more than two, and regardless of the number of longitudinal flow cell channels present, the present invention can be applied to ratio one or more sample containing flow cell channel signals to as few as one simultaneously recorded reference channel signal, thereby providing a double-beam-in-space electromagnetic radiation absorbance monitoring system, (for each sample channel), regardless of the actual number of sample channels present, in addition to as few as one reference channel.

Continuing, a method of determining a ratio of electromagnetic radiant powers ($P/P^0$), one thereof being associated with absorption of electromagnetic radiation by a sample (P) and the other thereof with a reference ($P^0$), comprises the steps of:

a. providing a multiple channel absorbance monitoring system as recited above;

b. causing an analyte containing fluid to flow into at least one of said longitudinal flow cell channels, or placing an at least partially transparent solid thereinto;

c. causing a beam of electromagnetic radiation from said source of electromagnetic radiation to pass through said at least one of said longitudinal flow cell channels which has analyte containing fluid or an at least partially transparent solid therewithin, as well as another beam of electromagnetic radiation from said source of electromagnetic radiation to pass through another of said longitudinal flow cell channels which does not have said analyte containing fluid or an at least partially transparent solid present therewithin;

d. causing said beams of electromagnetic radiation to exit said longitudinal flow cell channels which have analyte containing fluid or an at least partially transparent solid therewithin and which do not have said analyte containing fluid or an at least partially transparent solid present therewithin, such that said electromagnetic radiation beams which exit from both said longitudinal flow cell channels directly arrive at said detector chip at substantially different locations thereupon;

e. simultaneously, but separately monitoring the radiant power of at least two groupings of binned pixels in said detector chip, which two groupings of binned pixels each receive electromagnetic from substantially only one of each of said longitudinal flow cell channels, and forming a ratio of said radiant powers $((p)/(p^0))$.

With $((P)/(P^0))$ determined it is then possible to form the negative logarithm computation of absorbance and evaluation of unknown sample concentration via calibration with a standard sample and application of Beer's Law.

It is again noted that masking for defining a beam of electromagnetism entered to a longitudinal flow cell channel is typically be positioned between the source of electromagnetic radiation and the entry to a longitudinal flow cell channel, and that a filter for isolating wavelengths is typically positioned somewhere between the source of electromagnetic radiation and detector chip.

The present invention system also comprises a multiple longitudinal flow cell channel electromagnetic radiation monitoring system comprising:

a source of electromagnetic radiation;

a multiple-longitudinal flow cell channel system; and a detector chip;

longitudinal axes of said multiple-longitudinal flow cell channels in said multiple-longitudinal flow cell channel system being oriented substantially parallel to one another; said source of electromagnetic radiation simultaneously providing UV wavelength range electromagnetic radiation to at least two longitudinal flow cell channels in said multiple-longitudinal flow cell channel system a by selection from the group consisting of:

directly;

via optical fibers; and via beam expanding means;

said detector chip being of sufficient dimensions to simultaneously receive electromagnetic radiation from at least said at least two longitudinal flow cell channels in said multiple-longitudinal flow cell channel system via a selection from the group consisting of:

directly;

via light fibers; and via focusing means;

at least one of said longitudinal flow cell channels also having means for flowing analyte containing fluid through a portion thereof in the pathway of electromagnetic radiation entered thereinto;

each said longitudinal flow cell channel in said multiple-longitudinal flow cell channel cell system being constructed and oriented to direct electromagnetic radiation entered thereinto, or developed as a result of fluorescence caused thereby, to be directed to said detector chip such that electromagnetic radiation from at least two longitudinal flow cell channels arrives directly at said detector chip at substantially different locations thereupon;

said multiple-longitudinal flow cell channel electromagnetic radiation monitoring system detector chip having fluorophore material positioned with respect to detector elements thereof such that said detector elements are sensitized to UV.

Another present invention embodiment is a multiple longitudinal flow cell channel electromagnetic radiation fluorescence monitoring system which comprises:

a source of fluorescence causing excitation electromagnetic radiation;

a multiple-longitudinal flow cell channel system; and a detector chip;

longitudinal axes of said multiple-longitudinal flow cell channels in said multiple-longitudinal flow cell channel system being oriented substantially parallel to one another; said source of fluorescence causing electromagnetic radiation being oriented so as to provide beams of electromagnetic radiation directly into at least two of said longitudinal flow cell channels in said multiple-longitudinal flow cell channel system, said beams of electromagnetic radiation being directed longitudinally, (ie. along the axial flow axis), into said flow cell channels;

said detector chip being of sufficient dimensions to simultaneously directly receive fluorescence electromagnetic radiation exiting from said at least two longitudinal flow cell channels in said multiple-longitudinal flow cell channel system from a direction other than along the longitudinal axis direction of said at least two longitudinal flow cell channel;

at least two of said longitudinal flow cell channels of said multiple-longitudinal flow cell channel system having means for allowing fluorescent electromagnetic radiation to exit therefrom in a direction other than along the longitudinal direction of said at least one said longitudinal flow cell channel;

each longitudinal flow cell channel of said multiple-longitudinal flow cell channel system having means for entering fluorescence causing electromagnetic radiation from said source of fluorescence causing electromagnetic radiation, and at least one of said longitudinal flow cell channels also having means for flowing analyte containing fluid through a portion thereof in the pathway of said fluorescence causing electromagnetic radiation;

each said means for allowing fluorescent electromagnetic radiation to exit from said longitudinal flow cell channel in said multiple-longitudinal flow cell channel cell system being oriented to direct fluorescence electromagnetic radiation exiting therefrom, directly onto said detector chip such that fluorescence electromagnetic radiation exiting each longitudinal flow cell channels arrives directly at said detector chip at substantially different locations thereupon.

(Note a preferred arrangement provides for sample analyte containing fluid flow axially through a longitudinal flow cell with fluorescence excited by electromagnetic radiation entered in axial direction, being caused to exit obliquely to the longitudinal flow cell flow axis, and preferably radially, through the longitudinal flow cell wall or other means for allowing fluorescent electromagnetic radiation to exit therefrom).

A method of monitoring fluorescence comprises:

a. providing a multiple longitudinal flow cell channel electromagnetic radiation fluorescence monitoring system as described above;

b. causing an analyte containing fluid to flow into at least one of said longitudinal flow cell channels, or placing an at least partially transparent solid thereinto;

c. causing a beam of fluorescence causing electromagnetic radiation from said source thereof to pass through said at least two of said longitudinal flow cell channels, at least one of which has analyte containing fluid or an at least partially transparent solid therewithin;

d. causing induced fluorescence in said at least two channels to exit said at least two channels and enter said detector chip along a locus other than parallel to the longitudinal channel longitudinal direction, and such that said fluorescence electromagnetic radiation exiting from different longitudinal flow cell channels directly arrives at said detector chip at substantially different locations thereupon.

The present invention will be better understood by reference to the Detailed Description Section of this Specification, with reference to the Drawings.

SUMMARY OF THE INVENTION

A primary purpose and/or objective of the present invention is to teach application of single chip based detector means in combination with multiple channel electromagnetic radiation absorbance and fluorescence monitoring systems.

Another purpose and/or objective of the present invention is to teach application of a lumagen/flourophore to a single chip based detector system to sensitize detector elements thereof to UV wavelengths.

Another purpose yet and/or objective of the present invention is to teach application of single detector means in combination with multiple channel electromagnetic radiation absorbance or fluorescence monitoring systems, wherein the single detector means is a silicon chip selected from the group consisting of a linear or two dimensional:

128;
256;
512;
2048;
3072;
4096;

pixel or other available CCD or photo-diode pixel array which is positioned to directly receive electromagnetic radiation exiting from the longitudinal flow cell channels.

Yet another purpose and/or objective of the present invention is to teach formation of longitudinal flow cell channels in a multiple channel electromagnetic radiation absorbance or fluorescence monitoring system, by utilizing tube arrays or machining bores, (and optionally including sleeving in said bores), in a monolithic mass of material such as PEEK; fused silica; glass; titanium; and passivated stainless steel.

Another purpose and/or objective yet of the present invention is to disclose use of a single large area source of electromagnetic radiation, (as a preferred option to beam splitting means), which is of sufficient physical dimension to simultaneously provide electromagnetic radiation directly to all longitudinal flow cell channels in a multiple channel electromagnetic radiation absorbance or fluorescence monitoring system.

Another purpose and/or objective of the present invention is to disclose the use of a detector chip of sufficient dimensions to simultaneously directly receive electromagnetic radiation from at least two longitudinal flow cell channels in a multiple-longitudinal flow cell channel system at different locations thereon.

Still another purpose and/or objective yet of the present invention is to teach the use of a source of electromagnetic radiation having dimensions sufficient to simultaneously directly enter electromagnetic radiation to at least two longitudinal flow cell channels in a multiple-longitudinal flow cell channel system, in combination with the use of a detector chip of sufficient dimensions to simultaneously directly receive electromagnetic radiation from at least two longitudinal flow cell channels in a multiple-longitudinal flow cell channel system.

Another purpose and/or objective yet of the present invention is to, in combination with a multiple-longitudinal flow cell channel system, disclose the use of a source of electromagnetic radiation comprising a beam expander, beam splitter or multiple fiber optic subdivision or imaging lenses etc., alone or in combination, to provide electromagnetic radiation to all present longitudinal flow cell channels from a small source of electromagnetic radiation.

Yet another purpose and/or objective yet of the present invention is to, in combination with a multiple-longitudinal flow cell channel system, disclose the use of multiple fiber optics or imaging lenses etc., alone or in combination, to provide electromagnetic radiation from present longitudinal flow cell channels to a small detector chip.

Other purposes and/or objectives will become apparent from a reading of the Specification and accompanying claims.

DETAILED DESCRIPTION

Figure 1A:
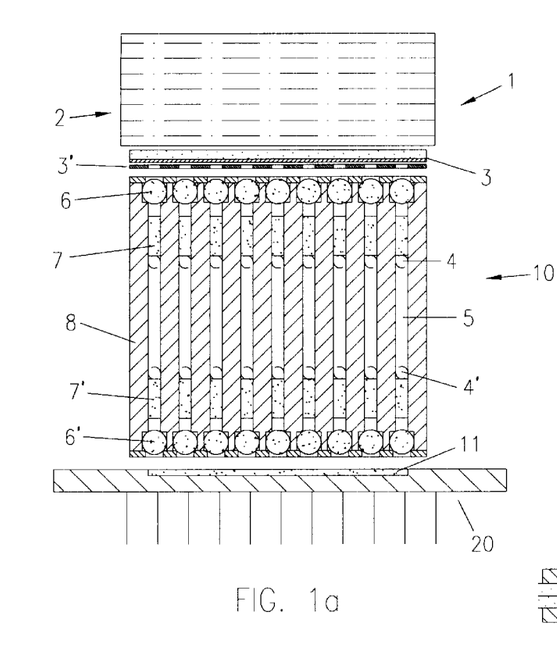
FIG. 1a shows a top cross-sectional of a present invention multiple-longitudinal flow channel electromagnetic radiation absorbance monitoring system (1) with a single source of electromagnetic radiation (2) and single detector chip (20).

Turning now to FIG. 1a, there is shown a top cross-sectional of a present invention double-beam-in-space elec tromagnetic radiation absorbance monitoring (1) system comprising:

a source of electromagnetic radiation (2);
a multiple-longitudinal flow cell channel system (10); and
a detector chip (20).

The longitudinal axes of said multiple-longitudinal flow cell channels in said multiple-longitudinal flow cell channel system (10) are shown to be oriented substantially parallel to one another. Each longitudinal flow cell channel (5) of the multiple-longitudinal flow cell channel system (10) has means for directly entering an electromagnetic radiation beam from said source of electromagnetic radiation along the longitudinal direction thereof, and at least some of said longitudinal flow cell channels also have means for flowing analyte containing fluid through a portion thereof (4) (4') which is in the pathway of said electromagnetic radiation. Each said longitudinal flow channel (5) in said multiple-longitudinal flow cell channel cell system (10) is oriented to direct electromagnetic radiation entered directly thereinto from said source of electromagnetic radiation (2), after it passes essentially longitudinally through said longitudinal flow cell channel (5), directly onto said detector chip (20) such that electromagnetic radiation passing through at least two longitudinal flow cell channels arrive at said detector chip at substantially different locations thereupon, in the active component, (eg. Photo-diode or CCD), containing region (11) thereof. It is to be specifically appreciated that said detector chip (20) is of sufficient dimensions to simultaneously directly receive electromagnetic radiation, in the active region thereof (11), from all of the shown longitudinal flow cell channels (5) in said multiple-longitudinal flow cell channel system (10). Typical present invention preferred Detectors are semiconductor chips such as are commonly employed in Fax and Bar Code Reading Machines, with typical dimensions of one-dimensional arrays utilized being twenty-eight (28) mm by two-hundred (200) microns. It is specifically noted that the present invention teaches coating said semiconductor chips, preferably the Detector Elements thereof directly, with a lumagen which sensitizes them to UV wavelengths, such as for instance 254 nm.

Note specifically that said source of electromagnetic radiation (2) is of sufficient physical dimension to provide electromagnetic radiation directly to all longitudinal flow cell channels (5) in said multiple-longitudinal flow cell channel system (10). This avoids the necessity to apply source electromagnetic radiation radiant power decreasing beam splitting means. Said source electromagnetic radiation (2) can be a mercury vapor discharge lamp such as available from BHK, Inc. in Ponoma, Calif., under the name "ANALAMP", which has outer dimensions of approximately two (2) inches by five (5) millimeters.

A preferred embodiment of said present invention multiple channel electromagnetic radiation absorbance monitoring system (1) has at least eight, (preferably nine, where one is a applied to monitor a standard), longitudinal flow cell channels (5) present through a monolithic mass of material (8), each of said at least eight longitudinal flow cell channels (5) optionally having two lengths of quartz rod (7) (7') embedded therewithin in a manner which seals a length of said longitudinal flow cell channel (5) therebetween, and each of said at least nine longitudinal flow cell channels further optionally having, as means for entering and exiting electromagnetic radiation, sapphire ball/lens (6) (6') embedded therein, one at each end thereof, with a void space (12), (see FIG. 1d), optionally being present centrally between each sapphire ball/lens (6) (6') and the nearest length of quartz rod (7) (7'), when said quartz rods are present. Means for flowing analyte containing fluid through each longitudinal flow cell channel preferably comprise inlet and outlet access channels (4) (4') which have oblique to perpendicular access to said longitudinal flow cell channel (5), (see FIG. 1e), shown otherwise sealed centrally between said two lengths of quartz rod (7) (7') therein; and the sapphire ball (6) at one end of said at least eight or nine longitudinal flow cell channels being positioned to receive and collimate electromagnetic radiation directly from said source of electromagnetic radiation, and the sapphire ball/lens (6') at the other end of said at least eight or nine longitudinal flow cell channels being positioned to de-collimate, (focus), and direct electromagnetic radiation directly to said detector chip (20).

Figure 8:
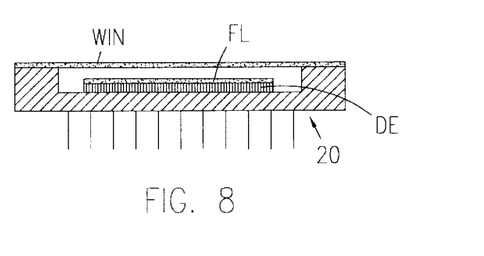
FIG. 8 demonstrates the presence of lumagen or other fluorophore (FL) present on the detector elements (DE'S) of a detector chip (20) as applied in the present invention.

FIG. 1a also show the preferred practice of placing an electromagnetic radiation wavelength filter (3) adjacent to an at least two hole mask (3') between the source (2) and sapphire balls (6). Said filter (3) can, however, be placed anywhere between the source (2) and detector chip (20). Further, as demonstrated in FIG. 8, said detector chip detector elements can be thinly, (eg. 500–10,000 Angstroms), coated with a fluorescing material, for instance a lumagen or other fluorophore, directly on the detector pixel elements to effect UV sensitization and secondarily to effect constant wavelength response electromagnetic radiation entry to said detector elements in region (11) of detector (10). (Note, it has been found that optimum practice involves removing the visible transparent, (typically glass), protective cover from standard monolithic CCD or photo-diode etc. detector chips, and applying fluorescing material directly to the detector elements therewithin), followed by replacing the original visible transparent cover with a UV transparent cover, (eg. made of for instance, fused silica). Note that FIG. 8 demonstrates typical construction of a single chip detector (20) and the preferred location of lumagen or other fluorophore (FL) present on the detector elements (DE'S) thereof as applied in the present invention. FIG. 8 further indicates window (WIN), which is not that provided with typical low cost detectors available for application in Fax machines and in Bar Code Readers etc., but rather is UV transparent. It is specifically stated that the action of the lumagen/fluorophore is to change the wavelength of incoming UV electromagnetic radiation to visible wavelengths to which the detector is sensitive, by well known fluorescing action.

Figure 1B:
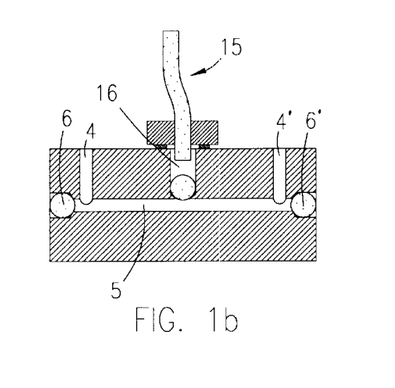
FIG. 1b shows a single longitudinal flow cell channel (5) with an additional accessing means (15) (16) to view axially excited, radially emitted fluorescence.

FIG. 1b demonstrates a modification of the FIG. 1a embodiment, wherein an essentially radially oriented optical fluorescence exit means (15) (16) from said longitudinal flow cell channel (5) is further present. As discussed with respect to FIG. 2a, said arrangement is useful in applications wherein radially accessed fluorescence is induced in longitudinal flow cell channel(s) (5) by longitudinally, (eg. axially), entered electromagnetic radiation. Note also that FIG. 1b demonstrates a case where quartz rods (7) (7') are not present, and flow sealing and electromagnetic radiation entry and exit is shown as by means of embedded sapphire balls/lenses.

Figure 1C:
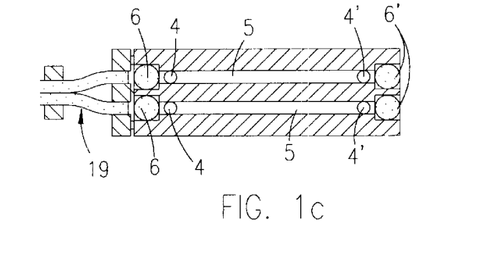
FIG. 1c shows a bundle of optical fibers (19) providing subdivided beams of electromagnetic radiation from a source of electromagnetism, to multiple-longitudinal flow cell channels.

FIG. 1c shows a bundle, (eg. demonstrated as two), of optical fibers (19) providing subdivided beams of electromagnetic radiation from a source of electromagnetism, to multiple-longitudinal flow cell channels (5). Note that while sapphire balls/lenses (6) are shown adjacent to the separated ends of fiber optics (19), in some embodiments, where electromagnetic radiation collimation is not required, they can be eliminated, with the light fibers (19) serving as sufficient sealing means.

Figure 1D:
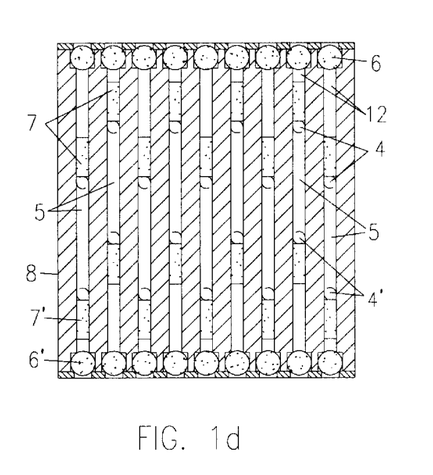
FIG. 1d shows a monolithic mass of material (8) with nine longitudinal flow cell channels (5) present therein much as in FIG. 1a, but shows with the access channels (4) (4') staggered in position, to allow easier flow connections with less crowding of attaching means.

FIG. 1d shows a monolithic mass of material (8), with each of said at least eight, (or nine), longitudinal flow cell channels (5) present therein much as in FIG. 1a, but it is to be noted that the two access channels (4) (4') which have oblique to perpendicular access to a longitudinal flow cell channel (5) are staggered in position, one adjacent longitudinal flow cell channel (5) to another. This is actually preferred as it avoids physical interfacing access problems, (mechanical interference of tapered holes and fittings), which can result where individual flow plumbing connections to the two access channels (4) (4') means of one channel are adjacent to those of another channel, as is the case shown in FIG. 1a.

Figure 1E:
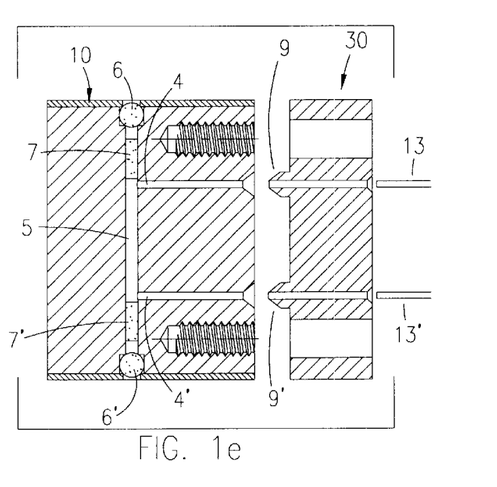
FIG. 1e shows a side view of one longitudinal flow cell channel (5) and the two associated access channels (4) (4').

FIG. 1e shows a side cross-sectional view, (taken vertically in FIG. 1a through a longitudinal flow cell channel (5)), of one longitudinal flow cell channel (5) and the two associated access channels (4) (4'). Note that a Compression Block (30) is shown configured to be screwed onto the monolithic multiple-longitudinal flow cell channel system (10), such that a sealing ferrule (9) (9') interconnection is achieved for tubes (13) (13') to be passed therethrough into access bores (4) (4'). Portion (30), it should be appreciated, is typically applied to a FIG. 1a configuration where access channels (4) (4') which have oblique to perpendicular access to adjacent longitudinal flow cell channel (5) are not in a staggered in position. The one-piece Compression Block (30) arrangement for providing access to longitudinal flow cell channel(s) (5) is particularly useful in providing easy access to longitudinal flow cell channel(s) present in a multiple-longitudinal flow cell channel system (10) formed in a monolithic mass of material (8).

Note specifically that the quartz rods (7) (7') can be absent in an alternative simplified embodiment, (demonstrated by FIG. 1b), with "press-in" sapphire ball/lens (6) (6') serving as both electromagnetic radiation directing and channel sealing means. In a further modification, the sapphire ball/lens and quartz rods can be replaced with fiber optics ends which are embedded at the ends of the longitudinal flow cell channels (5), (note the fiber optics are not directly shown, but conceptually a continuous combined (6) and (7) or (6') and (7') are to be interpreted as a length of fiber optic to disclose this embodiment). Further, where fiber optics are present, a remote end of a formed bundle thereof can be positioned near a smaller source of electromagnetic radiation than is shown in FIG. 1a. Two fibers from such a bundle of fibers (19) are demonstrated in FIG. 1c.

It is also noted that while access channels (4) (4') are typically utilized to enter and exit analyte containing gas or liquid fluid into longitudinal flow cell channels (5), it is, of course, conceivable to apply said access channels (4) (4') to enter at least partially transparent solids into the longitudinal flow cell channels (5), for instance where particles are dispersed in a fluid suspension.

Figure 2A:
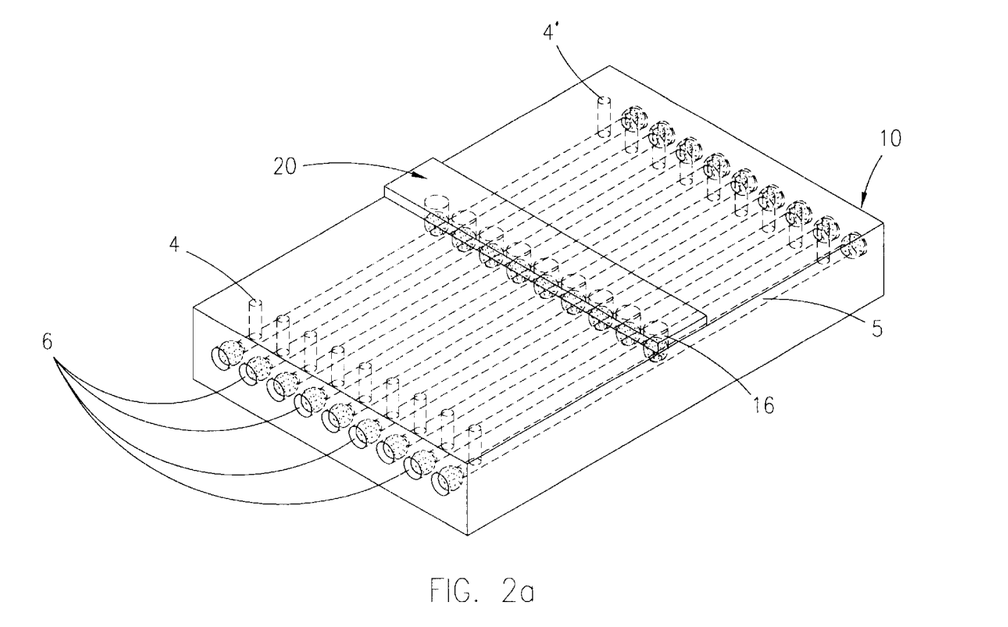
FIG. 2a shows a perspective view of a present invention multiple longitudinal flow cell channel electromagnetic radiation absorbance monitoring system (10) with the detector (20) positioned for use in detecting induced fluorescence electromagnetic radiation.

FIG. 2a shows a perspective view of a present invention multiple longitudinal flow cell channel electromagnetic radiation monitoring system (10) with the detector (20) positioned for use in detecting induced fluorescence electromagnetic radiation. Shown are sapphire ball/lens (6) (6') for each longitudinal flow cell channel (5) Note that as Indicated in FIG. 1b, longitudinal flow cell channel (5), radially oriented optical fluorescence exit means (16) is shown and serves to allow fluorescence electromagnetic radiation induced in longitudinal flow cell channels (5) to enter detector (20), when it is positioned as shown. Each longitudinal flow cell channel (5) provides fluorescence electromagnetic radiation to a different location on said detector (20). Again, the longitudinal axes of said multiple-longitudinal flow cell channels in said multiple-longitudinal flow cell channel system are oriented substantially parallel to one another, and in use a source of fluorescence causing electromagnetic radiation is oriented so as to provide beams of electromagnetic radiation directly into at least two of said longitudinal flow cell channels in said multiple-longitudinal flow cell channel system, said beams of electromagnetic radiation being directed longitudinally into said flow cell channels. The detector chip (20) is of sufficient dimensions to simultaneously directly receive fluorescence electromagnetic radiation exiting from said at least two longitudinal flow cell channels (5) in said multiple-longitudinal flow cell channel system from a direction other than along the longitudinal axis direction of said at least two longitudinal flow cell channels, (eg. radially via longitudinal flow cell channel optical fluorescence exit means (16) access and upward in FIG. 2a). That is, at least two of said longitudinal flow cell channels of said multiple-longitudinal flow cell channel system have optical fluorescence exit means (16) for allowing fluorescent electromagnetic radiation to exit therefrom in a direction other than along the longitudinal direction of said at least one said longitudinal flow cell channel. Each longitudinal flow cell channel (5) of said multiple-longitudinal flow cell channel system has means (6) for entering fluorescence causing electromagnetic radiation from said source of fluorescence causing electromagnetic radiation, and at least one of said longitudinal flow cell channels (5) also having means (4) (4') for flowing analyte containing fluid through a portion thereof in the pathway of said fluorescence excitation causing electromagnetic radiation.

Figure 2B:
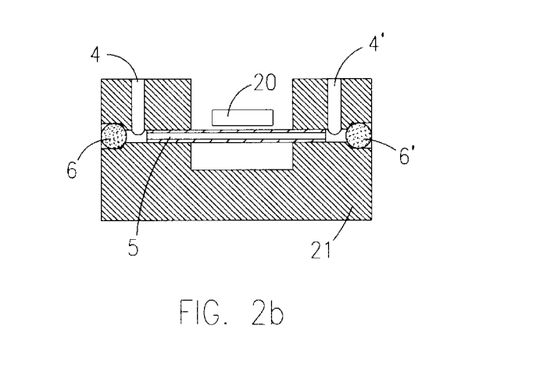
FIG. 2b shows, in a side elevational view, a variation of FIG. 2a, wherein longitudinal flow cell channels (5), (only the rightmost in FIG. 2a is visible), are each a separate tube, and in which detector chip (20) is placed adjacent to said separate tubes.

FIG. 2b shows, in a side elevational view, a variation of FIG. 2a, wherein longitudinal flow cell channels (5), (note, only the rightmost tube in FIG. 2a is visible in FIG. 2b), are each a separate tube, and in which detector chip (20) is placed adjacent to, (atop in FIG. 2b), said separate tubes. This variation comprises tube holding means (21) in place of the monolithic mass (10), and thus eliminates the need to provide the FIG. 2a radially oriented optical fluorescence exit means (16), which increases the length of a longitudinal flow cell channels (5) over which electromagnetic radiation can be entered to detector (20), (eg. over the length of an adjacent tube encountered by detector elements in detector (20)). Said FIG. 2b embodiment is also within the scope of the present invention.

Figure 3A:
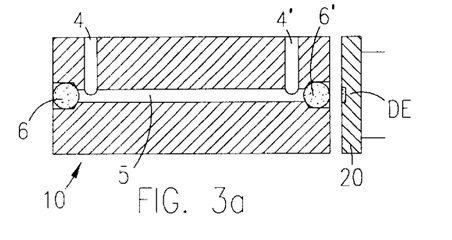
FIG. 3a shows a side view of a present invention multiple longitudinal flow cell channel electromagnetic radiation absorbance monitoring system (10) with the detector (20) positioned to detect absorbance electromagnetic radiation.

FIG. 3a shows a side view of a FIG. 1a present invention multiple longitudinal flow cell channel electromagnetic radiation absorbance monitoring system (10) with the detector (20) positioned for use in detecting electromagnetic radiation absorbance.

It should be appreciated that a FIG. 2a embodiment can be applied in monitoring absorbance of electromagnetic radiation where a detector (20) is positioned as shown in FIG. 3a.

Figure 3B:
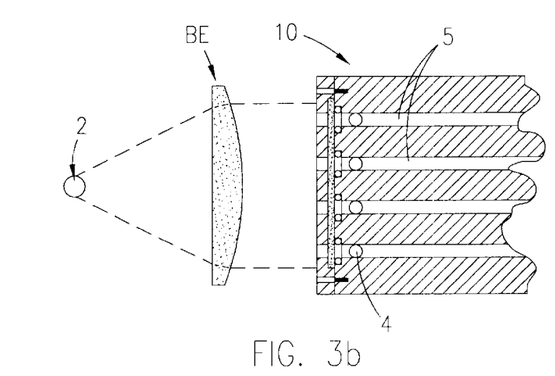
FIG. 3b shows use of a Beam Expander (BE) to provide a present invention multiple longitudinal flow cell channel electromagnetic radiation monitoring system (10) with a beam of electromagnetic radiation, from a small area source thereof, of sufficient area to enter all longitudinal flow cell channels (5).

FIG. 3b shows use of a Beam Expander (BE) to provide a present invention multiple longitudinal flow cell channel electromagnetic radiation monitoring system (10) with a beam of electromagnetic radiation, from a small area source thereof, of sufficient area to enter all longitudinal flow cell channels (5).

Figure 3C:
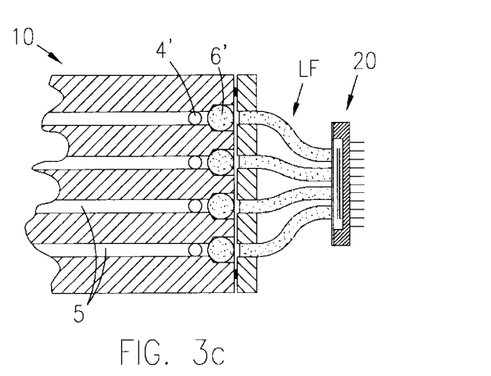
FIG. 3c shows use of a Light Fibers (LF) to provide a present invention multiple longitudinal flow cell channel electromagnetic radiation monitoring system (10) with beams of electromagnetic radiation from all longitudinal flow cell channels (5), onto a small area detector chip.

FIG. 3c shows use of a Light Fibers (LF) to provide a present invention multiple longitudinal flow cell channel electromagnetic radiation monitoring system (10) with beams of electromagnetic radiation from all longitudinal flow cell channels (5), onto a small area detector chip.

Figure 3D:
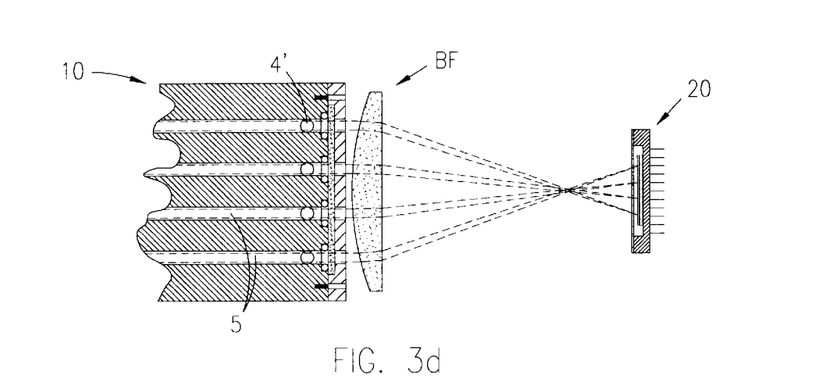
FIG. 3d shows use of a Beam Focusing means (BF) to provide a present invention multiple longitudinal flow cell channel electromagnetic radiation monitoring system (10) with beams of electromagnetic radiation from all longitudinal flow cell channels (5), onto a small area detector chip.

FIG. 3d shows use of a Beam Focusing means (BF) to provide a present invention multiple longitudinal flow cell channel electromagnetic radiation monitoring system (10) with beams of electromagnetic radiation from all longitudinal flow cell channels (5), onto a small area detector chip.

The use of Light Fibers to enter electromagnetic radiation to a enter electromagnetic radiation to multiple channels of a present invention multiple longitudinal flow cell channel electromagnetic radiation monitoring system (10), was demonstrated in FIG. 1c, for a two channel system.

(Note FIGS. 3b–3d demonstrate a present invention multiple longitudinal flow cell channel electromagnetic radiation monitoring system (10) with four longitudinal flow cell channels present).

Figure 4:
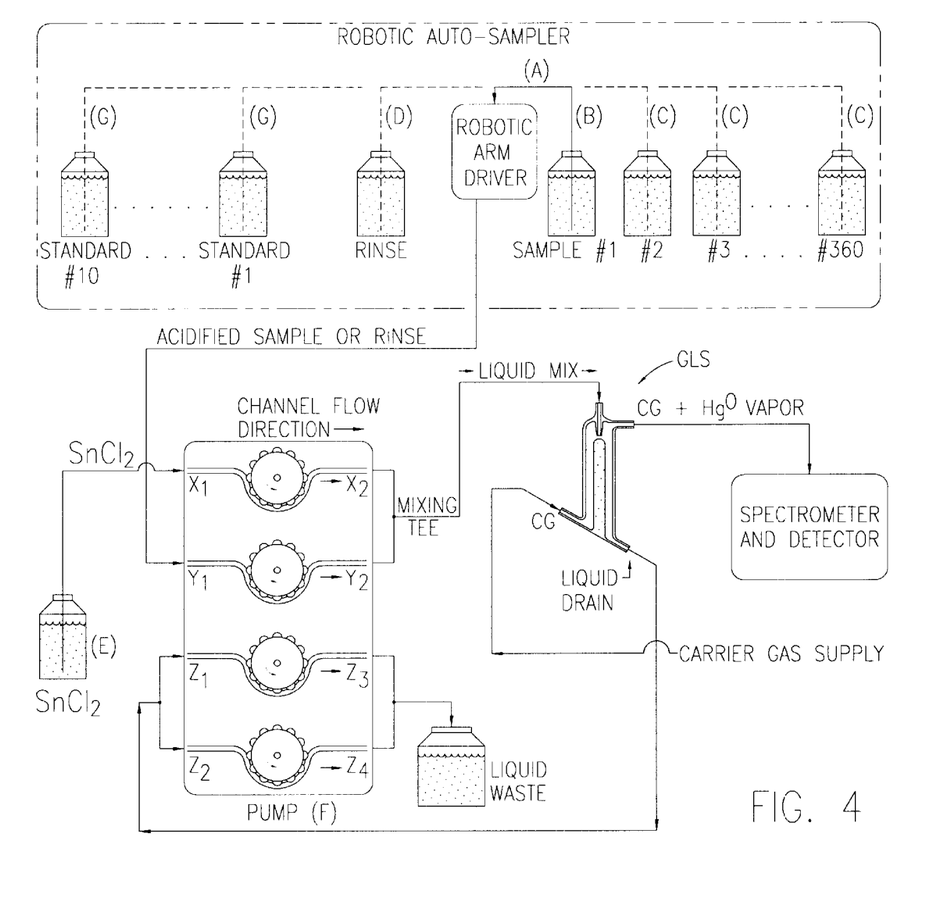
FIG. 4 shows FIG. 7 from U.S. Pat. No. 5,792,663 to Fry et al. to demonstrate application of a present invention at the location identified as "Spectrometer and Detector" as a mercury analyzer for liquids.
Figure 5:
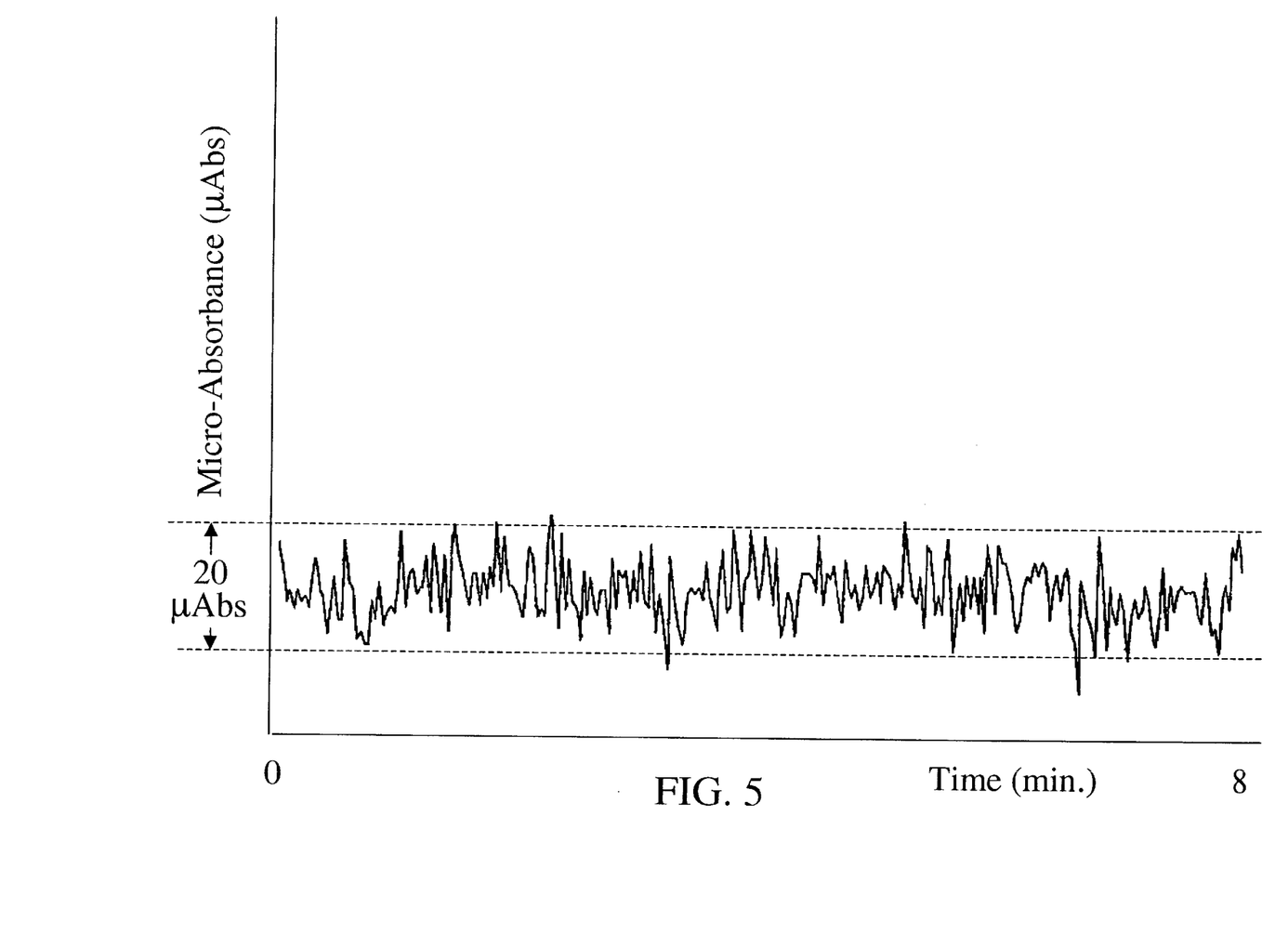
FIG. 5 shows a baseline noise of about 20 micro-Absorbance-units, with vapors from blank solution flowing through a longitudinal flow cell channel.
Figure 6:
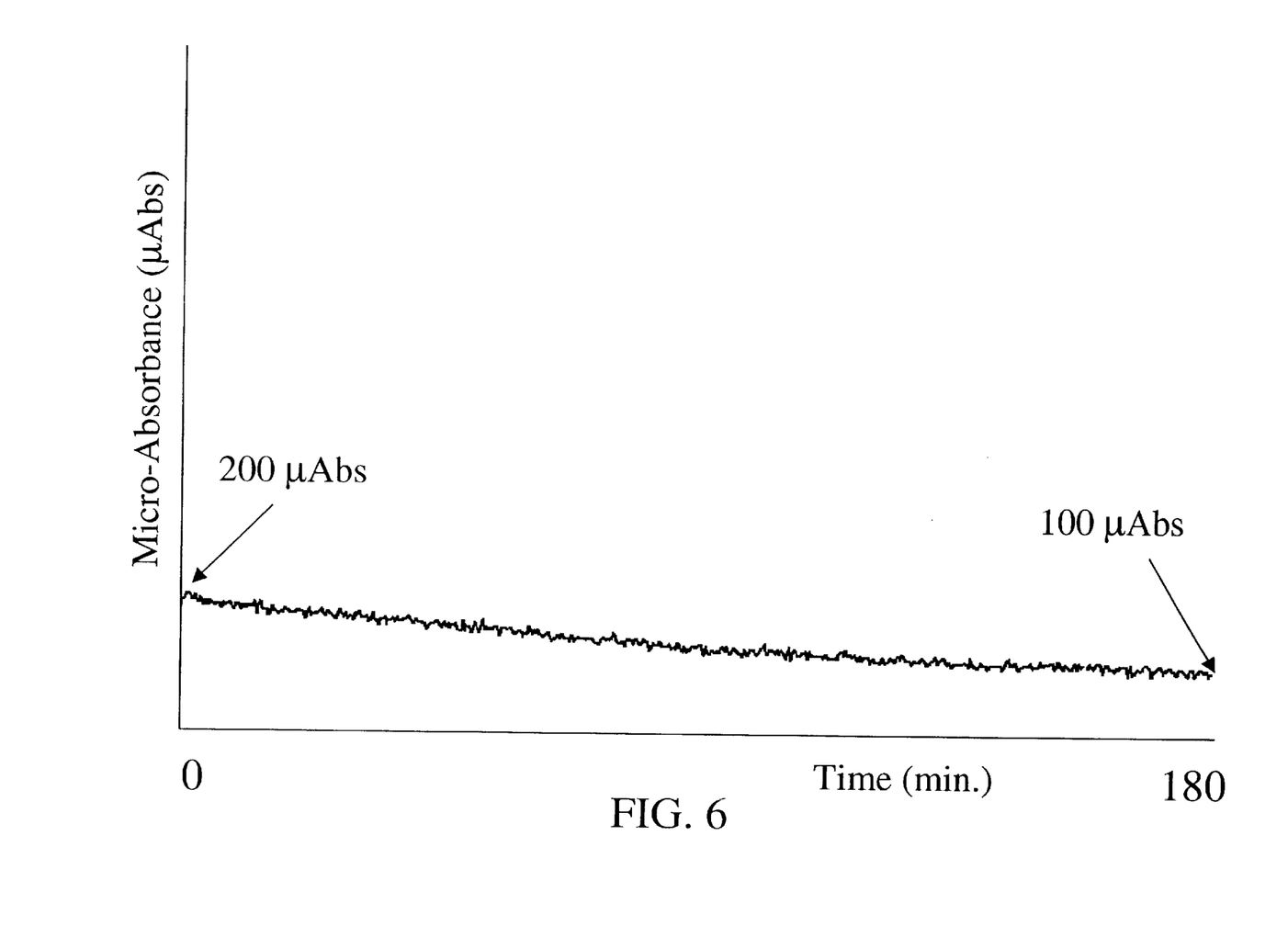
FIG. 6 shows double-beam-in-space baseline drift over a 3 hour period.
Figure 7:
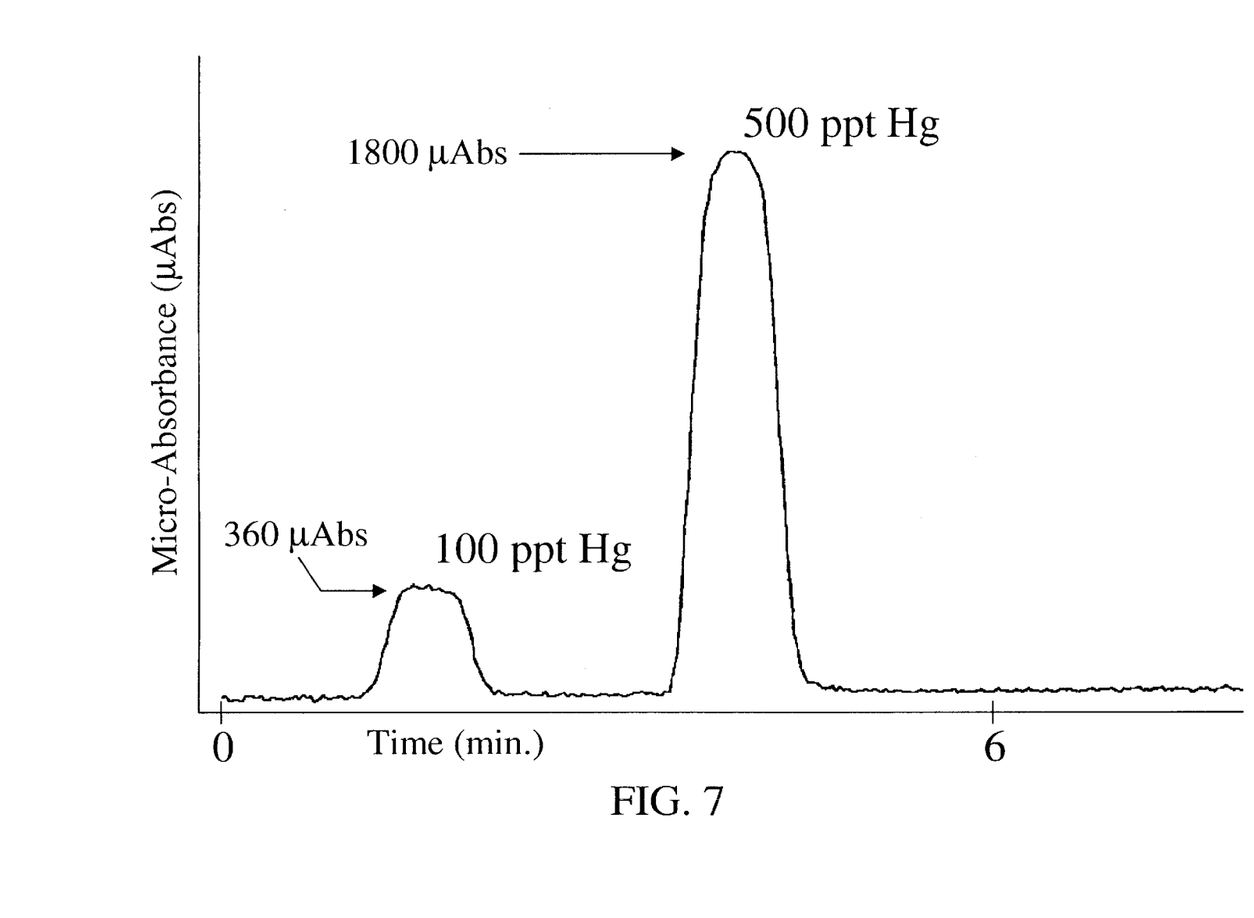
FIG. 7 shows a tracing indicating the monitoring of both 100 and 500 parts per trillion (PPT) mercury in a water sample medium.

As a specific example of application of the present invention in the context of the monitoring mercury presence in a liquid media, a two flow cell channel present invention system was applied in a system as described in Patent to Fry, U.S. Pat. No. 5,792,663, (said 663 Patent being incorporated by reference herein), in the location of the of the spectrometer and detector in FIG. 7 therein, which 663 Patent FIG. 7 is repeated herein as FIG. 4. Briefly said 663 Patent describes application of Stannous Chloride to $Hg^+$ containing aqueous solutions to provide $Hg^0$ in suspension, and the flow of the resulting mixture over a large area providing evaporation enhancing means which positions, in close proximity, a flow of carrier gas that delivers evaporated volatile components, (eg. $Hg^0$ vapor), to an analysis system, (eg. one channel of a two channel present invention multiple channel electromagnetic radiation absorbance monitoring system). The reader is referred to the 663 Patent for a detailed description, but briefly FIG. 4 herein indicates that $SnCl_2$ and Liquid Analyte containing Standards and Samples from a multiplicity of sources, via a Robotic Auto-Sampler, are sequentially entered to a Gas-Liquid Separator (GLS), with ($Hg^0$) vapors produced thereby being entered to a Spectrometer and Detector. It is also noted that the 663 Patent basically describes the CETAC Technologies M6000A Photometric Mercury Analyzer, which to date has typically comprised two separate Photovoltaic Detectors in the Spectrometer and Detector location shown in FIG. 4 herein. For the purposes of testing the present invention the Spectrometer and Detector indicated in FIG. 4 herein was constructed as a present invention multiple channel electromagnetic radiation absorbance monitoring system in combination with a Fluorophore coated Sony 2048 Pixel array chip positioned to directly intercept electromagnetic radiation from both sample vapor containing, and reference vapor flow channels. Note that a mercury detection of 6 Parts per Trillion, fine tuned to 4.2 Parts per Trillion was achieved using the present invention multiple channel electromagnetic radiation absorbance monitoring system at the location of the Spectrometer and Detector, shown in FIG. 4 herein and from analog chart recorder data obtained therefrom. FIG. 5 shows an analog baseline noise of about 20 micro-Absorbance-units, and FIG. 6 shows baseline drift over a 3 hour period. FIG. 7 shows a tracing indicating the monitoring of 100 parts per trillion (PPT) and 500 (PPT) ($Hg^{2+}$). Subsequent digital integration experiments performed by a new CETAC M4000 present invention double-beam-in-space spectrometer yielded a worse average mercury detection limit of 1.1 (PPT). A single-beam comparison yielded a worse average of 3.5 (PPT) mercury, hence an approximate 3-fold improvement for the present invention double-beam-in-space invention.

It is further disclosed that a modified present invention multiple channel electromagnetic radiation absorbance monitoring system can include additional means for detecting fluorescence induced in analyte entered to a present invention system channel, by axially applied electromagnetic radiation similar to as described in U.S. Pat. No. 6,008,055 to Zhu, for single flow chambers. Such means can be, for instance, an additional, centrally located, bore obliquely to perpendicularly entered into a longitudinal flow cell channel, in which is present, for instance, a sealing fiber optic. In use, excitation electromagnetic radiation is entered axially, much as already described in this Specification, but it is applied to induce fluorescence which is then radially monitored by the additional fiber optic, in place of monitoring axially exiting electromagnetic radiation. FIGS. 1b and 2a demonstrate this modification. FIG. 1b demonstrates addition of Optical Fiber (15) electromagnetic radiation transporting means which extends therefrom in combination with a longitudinal flow cell channel (16) access means, shown with a sapphire ball/lens present as sealing means. FIG. 2a demonstrates placement of a detector (20) to directly intercept induced and radially emitted fluorescence electromagnetic radiation, from a multiplicity of longitudinal flow cells.

Also, while a preferred source of electromagnetic radiation is a mercury lamp, said source of electromagnetic radiation can be selected, for instance, from the group consisting of:

mercury vapor lamp;
tungsten filament bulb;
quartz-halogen bulb
Xenon flash lamp;
deuterium lamp; and
argon ion laser, etc.

(Note in fluorescence inducing applications the sources of electromagnetic radiation will typically be narrowed to xenon lamps, laser systems and the like).

It is also to be understood that the terminology "each longitudinal flow cell channel of said multiple-longitudinal flow cell channel system having means for entering electromagnetic radiation directly from said source of electromagnetic radiation", is to be taken to means the an electromagnetic radiation wavelength filter might be present adjacent to said means and/or an at least two hole mask might be present thereat. Further, the terminology "electromagnetic radiation passing through at least two longitudinal flow cell channels arrives directly at said detector chip at substantially different locations thereupon" is to be interpreted to mean that means such as diffraction gratings or optics etc. are not present prior to the detector chip, except, again, for the possibility of the presence of a filter.

It is noted that the present invention finds application in mercury detection, and in combination with in high pressure liquid chromatography (HPLC) and in electrophoresis systems.

Finally, conception of the idea of applying of the system and methodology of U.S. Pat. No. 5,815,276 to Fry, to the present multiple longitudinal flow cell channel system is noted. Said 276 Patent involves decreasing sensitivity to internal reflection mediated system-element-parameter-change, by appropriate positioning of apertures.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the claims.

We claim:

1. A method of determining a ratio of electromagnetic radiation radiant powers one thereof being associated with absorption of electromagnetic radiation by a sample and the other thereof with absorption by a reference, said method comprising the steps of:

a providing a multiple-longitudinal flow cell channel electromagnetic radiation absorbance monitoring system comprising:
a source of electromagnetic radiation;
a multiple-longitudinal flow cell channel system; and
a detector chip;

longitudinal axes of said multiple-longitudinal flow cell channels in said multiple-longitudinal flow cell channel system being oriented substantially parallel to one another;

said source of electromagnetic radiation having dimensions sufficient to simultaneously directly enter electromagnetic radiation to at least two longitudinal flow cell channels in said multiple-longitudinal flow cell channel system;

said detector chip being of sufficient dimensions to simultaneously directly receive electromagnetic radiation from at least said at least two longitudinal flow cell channels in said multiple-longitudinal flow cell channel system;

each longitudinal flow cell channel of said multiple-longitudinal flow cell channel system having means for entering electromagnetic radiation directly from said source of electromagnetic radiation, and at least one of said longitudinal flow cell channels also having means for flowing analyte containing fluid through a portion thereof in the pathway of said electromagnetic radiation, each said longitudinal flow cell channel in said multiple-longitudinal flow cell channel cell system being oriented to direct electromagnetic radiation entered thereinto directly from said source of electromagnetic radiation, after it passes through said longitudinal flow cell channel, directly onto said detector chip such that electromagnetic radiation passing through at least two longitudinal flow cell channels arrives directly at said detector chip at substantially different locations thereupon;

b causing an analyte containing fluid to flow into at least one of said longitudinal flow cell channels;

c causing a beam of electromagnetic radiation from said source of electromagnetic radiation to pass through said at least one of said longitudinal flow cell channels which has analyte containing fluid therewithin, as well as another beam of electromagnetic radiation from said source of electromagnetic radiation to pass through another of said longitudinal flow cell channels which does not have said analyte containing fluid therewithin;

d causing said beams of electromagnetic radiation to exit said longitudinal flow cell channels which have analyte containing fluid therewithin and which do not have said analyte containing fluid therewithin, such that said electromagnetic radiation beams which exit from both said longitudinal flow cell channels directly arrive at said detector chip at substantially different locations thereupon;

e simultaneously, but separately monitoring the radiant power of at least two groupings of binned pixels in said detector chip, which two groupings of binned pixels each receive electromagnetic from substantially only one of each of said longitudinal flow cell channels, and forming a ratio of said radiant powers $((p)/(p^o))$.

2. A method of monitoring electromagnetic radiation radiant power, said method comprising the steps of:

a. providing a multiple-longitudinal flow cell channel electromagnetic radiation absorbance monitoring system comprising:
   a source of electromagnetic radiation;
   a multiple-longitudinal flow cell channel system; and
   a detector chip;
      longitudinal axes of said multiple-longitudinal flow cell channels in said multiple-longitudinal flow cell channel system being oriented substantially parallel to one another;
      said detector chip being of sufficient dimensions to simultaneously receive electromagnetic radiation from at least two longitudinal flow cell channels in said multiple-longitudinal flow cell channel system;
      each longitudinal flow cell channel of said multiple-longitudinal flow cell channel system being formed in a monolithic mass of material and having means for entering electromagnetic radiation from said source of electromagnetic radiation;
      at least one of said longitudinal flow cell channels also having means for placing a sample in the pathway of said electromagnetic radiation, each said longitudinal flow cell channel in said multiple-longitudinal flow cell channel cell system being oriented to direct electromagnetic radiation entered thereinto from said source of electromagnetic radiation, after it passes through said longitudinal flow cell channel, onto said detector chip such that electromagnetic radiation passing through at least two longitudinal flow cell channels arrive at said detector chip at substantially different locations thereupon;

b. causing a sample to be present in at least one of said longitudinal flow cell channels;

c. causing electromagnetic radiation from said source of electromagnetic radiation to pass through said at least two of said longitudinal flow cell channels which has said sample therewithin;

d. causing said electromagnetic radiation to exist said at least one longitudinal flow cell channel which has sample therewithin and another longitudinal flow cell channel therein, such that said electromagnetic radiation which exists from each said longitudinal flow cell channel arrives at said detector chip at substantially different locations thereupon;

e. simultaneously, but separately monitoring the radiant power of at least two locations on said detector chip, each of which two locations receive electromagnetic from substantially only one of each of said longitudinal flow cell channels.

* * * * *